(12) United States Patent
Kalmeta (10) Patent No.: US 9,180,319 B2
(45) Date of Patent: Nov. 10, 2015

(54) LASER ASSISTED PERIODONTIUM AND OSSEUS REGENERATION PROTOCOL

(71) Applicant: Margaret V. Kalmeta, Aptos, CA (US)

(72) Inventor: Margaret V. Kalmeta, Aptos, CA (US)

( * ) Notice: Subject to any disclaimer, the term of this patent is extended or adjusted under 35 U.S.C. 154(b) by 0 days.

(21) Appl. No.: 13/864,226

(22) Filed: Apr. 16, 2013

(65) Prior Publication Data

US 2014/0141389 A1 May 22, 2014

Related U.S. Application Data

(63) Continuation-in-part of application No. 13/078,757, filed on Apr. 1, 2011, now abandoned.

(51) Int. Cl.

| | |
|---|---|
| *A61Q 11/00* | (2006.01) |
| *A61K 8/41* | (2006.01) |
| *A61K 8/24* | (2006.01) |
| *A61C 19/06* | (2006.01) |
| *A61N 5/06* | (2006.01) |
| *A61C 1/00* | (2006.01) |
| *A61K 8/368* | (2006.01) |
| *A61K 8/44* | (2006.01) |
| *A61K 8/60* | (2006.01) |
| *A61K 8/20* | (2006.01) |
| *A61N 5/067* | (2006.01) |

(52) U.S. Cl.
CPC ............. *A61Q 11/00* (2013.01); *A61C 1/0046* (2013.01); *A61C 19/063* (2013.01); *A61K 8/20* (2013.01); *A61K 8/24* (2013.01); *A61K 8/368* (2013.01); *A61K 8/416* (2013.01); *A61K 8/44* (2013.01); *A61K 8/442* (2013.01); *A61K 8/606* (2013.01); *A61N 5/0603* (2013.01); *A61N 5/0613* (2013.01); *A61N 5/062* (2013.01); *A61N 2005/067* (2013.01); *A61N 2005/0659* (2013.01)

(58) Field of Classification Search
USPC ................ 433/216; 424/49, 54, 57
See application file for complete search history.

(56) References Cited

U.S. PATENT DOCUMENTS

| | | | |
|---|---|---|---|
| 7,107,996 B2 | 9/2006 | Ganz et al. | |
| 7,621,745 B2 | 11/2009 | Bornstein | |
| 2006/0210494 A1* | 9/2006 | Rabiei et al. | 424/57 |
| 2009/0087816 A1 | 4/2009 | Bornstein | |

OTHER PUBLICATIONS

Asai et al. "Maxillary Sinus Augmentation Model in Rabbits" Effect of Occluded Nasal Ostium on New Bone Formation. (2002) Clin. Oral Impl. Res. 13:405-409.
Goldstep—www..oralhealthjournal.com—Diode Lasers for Periodontal Treatment: The story so far. Publication Dec. 2009, p. 44-46.
Ozcelik—http://www.ncbi.nlm.nih.gov/pubmed/148081859—Enamel matrix derivative and low-level laser therapy in the treatment of intra-bony defects: a randomized placebo-controlled clinical trial—J. Clin. Periodontol. Feb. 2008 35 (2):56-147. Epub Dec. 13, 2007.

* cited by examiner

*Primary Examiner* — Lezah Roberts
(74) *Attorney, Agent, or Firm* — Lewis Kohn & Walker LLP; David M. Kohn; Kari Moyer-Henry (57) ABSTRACT

A method of treating gum disease using a soft tissue diode laser which generates a beam of light having a wavelength in the visible portion of the electromagnetic spectrum (400 nm-700 nm) at a laser power of 0.5 to 1.2 watts, used with intermittent stops to control tissue temperature, to decontaminate the gum tissue and biostimulate the periodontium non-surgically when used with a substrate, thus preventing the long junctional epithelium from migrating into the sulcus, preserving tissue height, and regenerating periodontium, the method comprising: placing the tip of the laser inside the sulcus; penetrating the entire sulcus by moving the laser light with intermittent stops to control tissue temperature vertically and horizontally throughout the sulcus; and placing a substrate in the sulcus prior to a blood clot forming, thus regenerating periodontium in the sulcus.

17 Claims, 9 Drawing Sheets

LASER ASSISTED PERIODONTIUM AND OSSEUS REGENERATION PROTOCOL

CROSS REFERENCES

This application is a Continuation-In-Part Patent Application claiming the benefit of priority under 35 U.S.C. 120 from U.S. patent application Ser. No. 13/078,757 filed Apr. 1, 2011, the entire contents of which are herein incorporated by reference.

FIELD OF THE INVENTION

The present invention relates generally to a method of treating gum diseases using a soft tissue diode laser which produces a beam of light having a wavelength in the visible portion of the electromagnetic spectrum (400 nm-700 nm). Optionally, the laser light utilizes green wavelength range (520-570 nm) at a laser power of 0.5 to 1.2 watts to treat gum disease.

BACKGROUND OF THE INVENTION

Laser Assisted Periodontium And Osseus Regeneration (LAPOR) is a protocol which is laser assisted with the use of a substrate such as but not limited the LAPOR periodontal solution, the LAPOR periodontal gel and the LAPOR substrate and thus causes an increase in cell attachment of epithelial cells, gingival fibroblasts, PDL fibroblasts and adhesion of osteogenic cells. This protocol has shown to increase the expression of transcription factors related to the differentiation of osteoblasts/cementoblasts as well as chondroblasts. Enhanced cell migration and proliferation appears to lead to accelerated wound fill rates in vitro using PDL fibroblasts, gingival fibroblasts and osteoblast-like cells.

A substrate such as the LAPOR periodontal solution, the LAPOR periodontal gel and the LAPOR substrate, used in the LAPOR protocol, stimulates total protein synthesis and the synthesis of specific extracellular matrix molecules. Studies that evaluate the bone remodeling regulation system indicate that enamel matrix proteins influence this by modulating the OPG and RANKI expression, thus indicating an indirect involvement in the bone remodeling process.

The soft tissue diode laser used produces a beam of light having a wavelength in the visible portion of the electromagnetic spectrum (400 nm-700 nm). Optionally, a beam of light having a wavelength in the green wavelength range (520-570 nm) at a laser power of 0.5 to 1.2 watts is used in the LAPOR protocol. It has been shown by the LAPOR protocol to biostimulate the healing and regenerative processes of the periodontium, including the biostimulation of new bone and its supporting elements. Previous studies have shown a positive healing effect of low power laser therapy (infrared range of a soft tissue diode laser) on tissue repair. Low power lasers, in the infrared range, have been shown to positively affect several indices of tissue repair. They biostimulate wound healing by acceleration of collagen synthesis, acceleration of inflammation, decrease of healing time, acquisition of strength. They biostimulate regeneration of tissue via elevated metabolic indices of ATP synthesis, elevated fibroblast proliferation, elevated collagen synthesis and increased indices of biomechanical aspects of tissue healing. The soft tissue diode laser used in the LAPOR protocol, biostimulates the healing response of the periodontium nonsurgically, and biostimulates the tissue regeneration of the periodontium, nonsurgically, and prevents long junctional epithelium from migrating downwards into the sulcus (a biomechanical aspect of tissue healing), thereby preserving the tissue height. A soft tissue diode laser used in the LAPOR protocol helps a substrate such as but not limited to enamel matrix proteins to stimulate total protein synthesis and the synthesis of extracellular matrix molecules, nonsurgically.

SUMMARY OF THE INVENTION

In an exemplary embodiment of the present invention, there is disclosed a method of treating gum disease using a soft tissue diode laser which generates a beam of light having a wavelength in the visible portion of the electromagnetic spectrum (400 nm-700 nm). Optionally, a beam of light having a wavelength in the green range (520-570 nm) at a laser power of 0.5 to 1.2 watts is used to decontaminate the gum tissue and to biostimulate healing and regenerate the periodontium (including cementum of the root surface), thus preventing long junctional epithelium from migrating downwards into the sulcus and thereby preserving the tissue height. The soft tissue diode laser also biostimulates the healing and regenerative response induced by a substrate, i.e. the LAPOR periodontal solution, the LAPOR periodontal gel and the LAPOR periodontal substrate, the method comprising: 1) placing the laser inside the sulcus; 2) penetrating the entire sulcus by moving the laser light intermittently vertically and horizontally throughout the sulcus; and 3) placing the substrate in the sulcus prior to a blood clot forming (which then increases cell attachment, adhesion, migration and proliferation).

In another embodiment of the present invention, there is disclosed a root/bone/cartilage conditioner comprised of EDTA 15%, calcium gluconate 20%, methylparaben, propylparaben, Ethanolamine as a buffering agent, carboxymethylcellulose, and green food coloring and sterile water.

In still another embodiment of the present invention, there is disclosed a first substrate comprised of: a combination of mono or disodium phosphate and sodium hydroxide in solution with a sodium content of 11 mg/100 g; 60% water; 9% Lysine; 9% Proline; 9% all other essential amino acids wherein the amino acids are chosen from the group consisting of Isoleucine, Leucine, Methionine, Phenylalanine, Threonine, Tryptophan, Valine, Histadine, Asparagine and Selenocysteine; 2% of all other non-essential amino acids wherein the amino acids are chosen from the group consisting of Alanine, Arginine, Aspartate, Cysteine, Glutamate, Glutamine, Glycine, Serine, Tyrosine and Pyrrolsine; 6.9% free bases wherein the free bases are chosen from the group consisting of adenosine, uridine, guanosine, iridin and cytidine; 2% phosphates wherein the phosphates are chosen from the group consisting of ADP, ATP and acetycholine; and 1% benzoic acid at a pH of 7.45.

In still another embodiment of the present invention, there is disclosed a second substrate comprised of tricalcium phosphate wherein the tricalcium phosphate is precipitated with calcium hydroxide/Claw oil; and hydroxyapatite crystals.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIG. 14 shows X-rays of tooth 15 of a patient from which measurements shown in FIG. 11 were collected. (a) shows tooth 15 before treatment. (b) shows tooth 15 at the October 2011 measurement following three treatments.

FIG. 15 shows X-rays of tooth 28 of a patient from which measurements shown in FIG. 12 were collected. (a) shows tooth 28 before treatment. (b) shows tooth 28 at the January 2011 measurement following four treatments.

FIG. 16 shows a panoramic X-ray of tooth 2, tooth 3 and tooth 15 of a patient from which measurements shown in FIG. 13 were collected. (a) shows the teeth before treatment. (b) shows the teeth at the July 2011 measurement.

DETAILED DESCRIPTION OF THE INVENTION

Definitions

As used herein, the term "gum disease" means periodontal disease which can lead to tooth loss and/or other health problems. Examples of periodontal disease include gingivitis, aggressive periodontitis, chronic periodontitis, periodontitis as a manifestation of systemic diseases, and necrotizing periodontal disease.

As used herein, the term "patient" means any individual suffering from a disease of the gums and in need of treatment for said gum disease.

As used herein, the term "locus" means an exact point of measurement within the sulcus or the immediate surrounding area.

As used herein, the term "substrate mixture" means the mixture of the first substrate and the second substrate disclosed herein for treatment of gum disease.

As used herein, the term "bone regeneration" means increasing the density of calcium at specific loci in or around the sulcus.

As used herein, the term "calcium density" means the measurement of calcium mass around a given loci.

The LAPOR protocol can be used in the treatment of gum disease by combining the most effective methods of treatment with the use of a special laser. Approximately 66% of the United States population has some form of gum disease. But many avoid seeking treatment because of the discomfort that often results from gum surgery. LAPOR provides a new choice. The LAPOR protocol is a treatment that is more effective as traditional periodontal surgery, and it is much more beneficial to the patient both in the short term and in the long run.

The LAPOR protocol takes only about an hour and only two short follow-up visits. Patients enjoy no downtime with recovery taking only 24 hours. This makes immediate return to work both possible and comfortable.

After having the LAPOR protocol performed, gum recession is minimal to none when compared to that which most often follows normal periodontal surgery. This, combined with new cementum formation on the roots, bone formation in previous defects, periodontal ligament formation tooth loss.

The special type of laser used in the LAPOR protocol is the diode, a semiconductor coherent light beam used on soft tissues. The laser light used has a wavelength in the visible portion of the electromagnetic spectrum, between 400 nm-700 nm wavelength. Optionally, the green range (520-570 nm) of the visible spectrum is utilized at a laser power of 0.5 to 1.2 watts, which disinfects the site, leaving the gum tissue bacteria free, and biostimulates healing; in conjunction with treatment with a substrate, the laser biostimulates regeneration of the periodontium. Traditional periodontal therapy removes tissue height of a tooth to reduce the pocket depths. The LAPOR protocol is a regenerative procedure. The patient does not lose tissue volume. Tissue volume is increased and bone is regenerated.

The green wavelength is ideally suited for soft tissue procedures since it is highly absorbed by hemoglobin and melanin. This gives the diode laser the ability to, in this case, target the soft tissues.

The use of the diode laser in conjunction with routine scaling and root planning is more effective than scaling and root planning alone. It enhances the speed and extent of the patients gingival healing and postoperative comfort. This is accomplished through laser bacterial reduction and biostimulation with a laser light having a wavelength in the visible portion of the electromagnetic spectrum, between 400 nm-700 nm wavelength. Optionally, the green range (520-570 nm) of the visible spectrum is utilized at a laser power of 0.5 to 1.2 watts.

Figure 1:
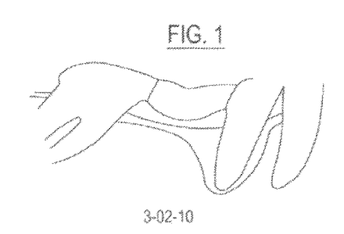
FIG. 1 shows an X-Ray view of a patient's teeth before treatment with a soft tissue diode laser before a substrate has been applied.
Figure 2:
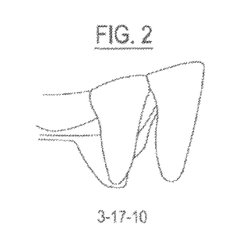
FIG. 2-7 show X-Ray views of the lower teeth of FIG. 1 after treatment with a soft tissue diode laser after treatment with a substrate.
Figure 3:
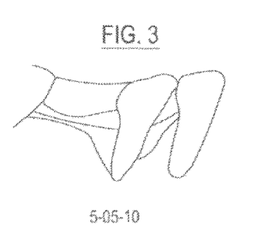
Figure 4:
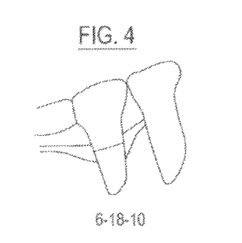
Figure 5:
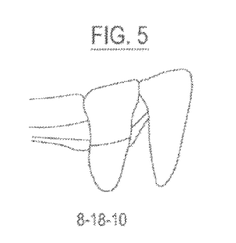
Figure 6:
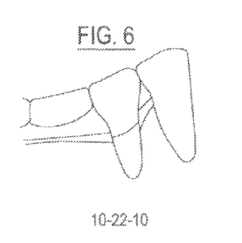
Figure 7:
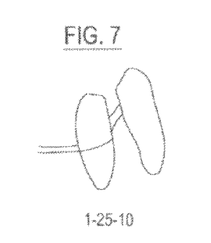
Figure 8:
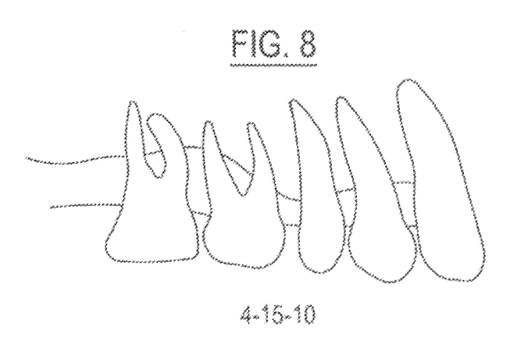
FIG. 8 shows an X-Ray view of the upper teeth before treatment with a soft tissue diode laser after treatment with a substrate.
Figure 9:
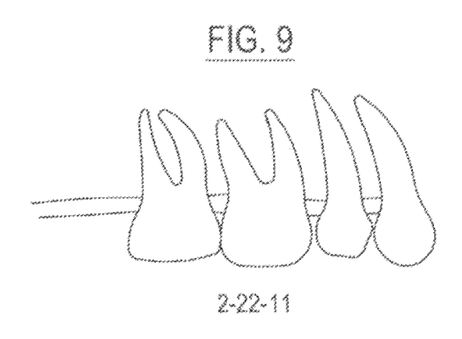
FIG. 9 shows an X-ray view of the upper teeth of FIG. 8 alter treatment with a soft tissue diode laser after treatment with a substrate.
Figure 10:
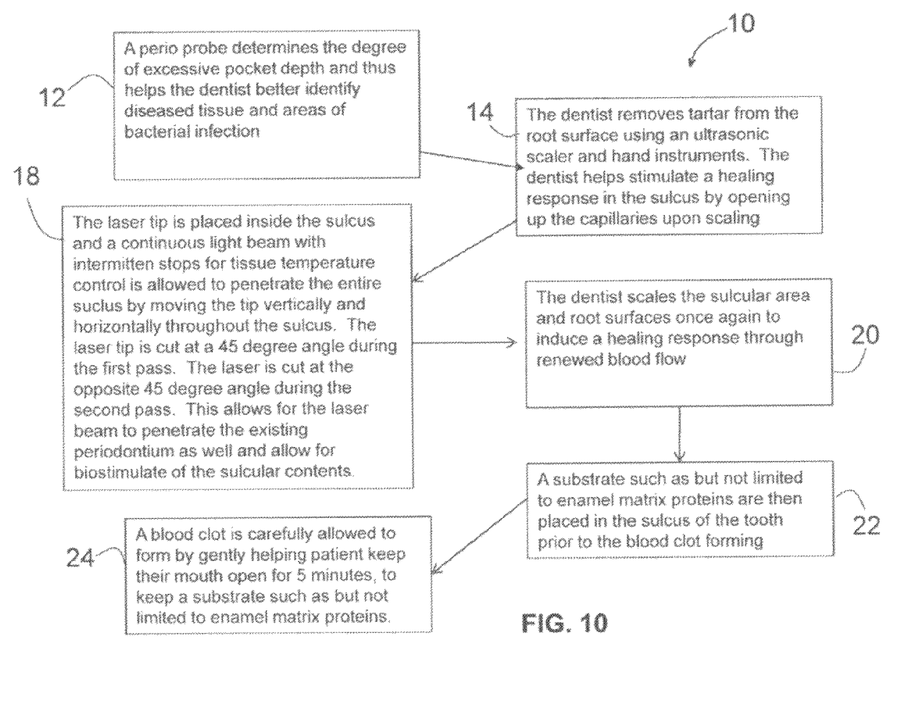
FIG. 10 shows a flow diagram of a method of using a soft tissue diode laser to treat gum disease in accordance with the principles of the invention.

Referring to FIG. 10, there is disclosed a method 10 of using a soft tissue diode laser which produces a beam of light, used intermittently, having a wavelength in the visible portion of the electromagnetic spectrum, between 400 nm-700 nm wavelength. Optionally, the green range (520-570 nm) of the visible spectrum is utilized at a laser power of 0.5 to 1.2 watts to treat gum disease. Starting at block 12, a perio probe determines the degree of excessive pocket depth and thus helps the dentist better identify diseased tissue and areas of bacterial infection. The dentist removes tartar from the root surface using an ultrasonic scaler and hand instruments, block 14. This action by the dentist helps stimulate a healing response in the sulcus by opening up the capillaries upon scaling. Going to block 18, the laser tip is placed inside the sulcus and a continuous light beam with intermittent stops for tissue temperature control is allowed to penetrate the entire sulcus by moving the tip vertically and horizontally throughout the sulcus. The laser tip is cut at a 45 degree angle during the first pass. The laser is cut at the opposite 45 degree angle during the second pass. This allows for the laser beam to penetrate the existing periodontium to decontaminate the tissue, as the heat of the targeted laser light kills the bacteria. This also allows for biostimulation of the sulcular contents. At block 20, the dentist scales the sulcular area and root surfaces once again to induce a healing response through renewed blood flow. Going to block 22, a substrate, such as but not limited to enamel matrix proteins, is then placed in the sulcus of the tooth prior to the blood clot forming and at block 24, a blood clot is carefully allowed to form by gently helping patient keep their mouth open for 5 minutes, to keep the substrate intact.

The LAPOR protocol is much less invasive than traditional surgery and offers advantages and benefits over its counterpart. Recovery time is much faster because most, if not all, damage to healthy tissue is avoided through the use of more advanced technology. Because the LAPOR protocol leaves healthy tissue intact, the height of the gums themselves around the teeth is much better preserved. The LAPOR protocol prevents long junctional epithelium from migrating downwards into the sulcus, thus preserving the tissue height and allowing for the regeneration of the periodontium.

Firstly, the root conditioner is applied to the sulcus. The root conditioner comprises the following at Table 1:

TABLE 1

| Component | |
|---|---|
| EDTA | 20-25 g. |
| Calcium gluconate | 10-20 g. |
| Methylparaben | .1-.9 g. |
| Propylparaben | .01-.1 g. |
| Ethanolamine | 2-8 mls. |
| Carboxymethylcellulose | 2-10 g. |
| Green food coloring | 1-2 drops |
| Sterile water | 100 mls. |

The conditioner is optionally rinsed out prior to application of additional substrates or laser light. Alternatively, the conditioner is left in the sulcus, with the laser light being applied prior to application of any substrate. In an alternative embodiment, the conditioner is left in with only one substrate applied prior to application of the laser light. Optionally, the conditioner is left in the sulcus and substrate is added prior to any application of laser light.

The placement of the substrate into the sulcus containing luminesced blood enables the luminesced blood to coagulate upon the substrate. The substrate contains building blocks for protein synthesis as well as substances used as energy for protein synthesis. The substrate also contains hard components that are able to be used by the body as a "lattice" for regeneration. The substrate also contains a slow release pH increasing agent to increase the pH for optimal regeneration while not "startling" the body such that it will have a negative reaction to the substrate.

Optionally, the liquid substrate is comprised of the following, per 1 L of solution, at Table 2:

TABLE 2

| Essential Amino Acids | % |
|---|---|
| Isoleucine | 1.125 |
| Leucine | 1.125 |
| Methionine | 1.125 |
| Phenylalanine | 1.125 |
| Threonine | 1.125 |
| Tryptophan | 1.125 |
| Valine | 1.125 |
| Histidine | 1.125 |
| Lysine | 9 |
| Non-Essential Amino Acids | % |
| Alanine | 0.25 |
| Arginine | 0.25 |
| Aspartate | 0.75 |
| Glutamate | 0.25 |
| Glycine | 0.25 |
| Serine | 0.25 |
| Proline | 9 |
| Phosphates | % |
| ADP | 0.667 |
| ATP | 0.667 |
| Acetylcholine | 0.667 |
| Free Bases | % |
| Adenosine | 1.725 |
| Uridine | 1.725 |
| Guanosine | 1.725 |
| Cytidine | 1.725 |
| Benzoic Acid | 1 |
| Sodium Chloride | 1.1 |
| Sterile water | 60 |
| Total: | 100 |

Optionally, the total sterile water component is adjusted 20% up or down, depending on the desired viscosity to be achieved.

In an alternative embodiment, the liquid substrate is comprised of the following, at Table 3:

TABLE 3

| Essential Amino Acids | Grams |
|---|---|
| Isoleucine | 11.25 |
| Leucine | 11.25 |
| Methionine | 11.25 |
| Phenylalanine | 11.25 |
| Threonine | 11.25 |

TABLE 3-continued

| | |
|---|---|
| Tryptophan | 11.25 |
| Valine | 11.25 |
| Histidine | 11.25 |
| Lysine | 90 |
| Non-Essential Amino Acids | Grams |
| Alanine | 2.5 |
| Arginine | 2.5 |
| Aspartate | 7.5 |
| Glutamate | 2.5 |
| Glycine | 2.5 |
| Serine | 2.5 |
| Proline | 90 |
| Phosphates | Grams |
| ADP | 7-8 |
| ATP | 7-8 |
| Acetylcholine | 6-7 |
| Free Bases | Grams |
| Adenosine | 13-14 |
| Uridine | 13-14 |
| Guanosine | 13-14 |
| Cytidine | 13-14 |
| Iridine | 13-14 |
| Benzoic Acid | 20 |
| Sodium Chloride | .1-.9 |
| Sterile water | .9-1.2 L |

Most preferred, the pH of the final solution for the liquid substrate should be 7.45 with a tendency to apply a basic pH.

An additional substrate may be applied, the additional substrate comprised of the following: a mixture of tricalcium phosphate and hydroxyapatite crystals. The tricalcium phosphate is precipitated with CaOH/devil's claw oil, in a preferred embodiment. Optionally, the additional substrate include 50% tricalcium phosphate/devil's claw oil precipitated with 50% porous hydroxyapatite crystals. The tricalcium phosphate crystals used are granules in the following sizes: 10-50 μm, 50-150 μm, 100-300 μm, 500-1000 μm, 1-3 mm and 3-6 mm. The tricalcium phosphate crystals may be dense or porous.

The additional substrate may be comprised of hydroxyapatite crystals of granules containing the following sizes: 10-50 μm, 50-150 μm, 100-300 μm, 500-1000 μm, 1-3 mm and 3-6 mm. The hydroxyapatite crystals may be dense or porous.

In the following examples, the conditioner is applied and is rinsed out. Optionally, the conditioner is left in the sulcus, as the conditioner allowed the micropores within the tooth structures to remain open.

After the conditioner is applied, the sulcus is biostimulated with a laser light. After this occurs, the liquid substrate is applied. Optionally, the additional substrate is applied.

EXAMPLES

I. Analysis of Tooth #15 at 12 Unique Loci

A patient's pocket depths at tooth 15 were measured at 12 separate loci. The root of the tooth was then scaled and planed to remove calculus build up on the root surface. After scaling and planning, bleeding occurs in the sulcus. The sulcus was allowed to air dry and immediately thereafter the conditioner is applied to the sulcus and left for 30 seconds before being rinsed with saline. The tooth was next scaled and planed again to renew blood flow. With blood pooling in the sulcus, the 45° laser tip was placed into the sulcus. The laser light used has a wavelength in the visible portion of the electromagnetic spectrum, between 400 nm-700 nm wavelength. The laser was emitted continuously with only intermittent stops for tissue temperature control. The laser was allowed to penetrate the entire sulcus by moving the tip vertically and horizontally throughout the sulcus for 30 second. The laser tip was cut to 45° in the opposite angle for the second pass into the sulcus and 90° for the third pass to allow the laser bean to penetrate the existing periodontium to decontaminate and biostimulate the sulcular contents.

In the meantime, the first substrate and the second substrate were mixed in a glass dish. Some of the patient's blood that has been treated with the laser light in the sulcus was also mixed in the glass dish. This mixture is then placed immediately into the sulcus upon mixture. Enough of the mixture was placed into the sulcus to fill the sulcus while ensuring the mixture stayed 3 mm below the top of the gingival margin and also remained immersed in blood. The patient's mouth was kept open for 5 minutes to ensure the newly formed blood clot containing the substrate mixture remained intact.

Figure 11:
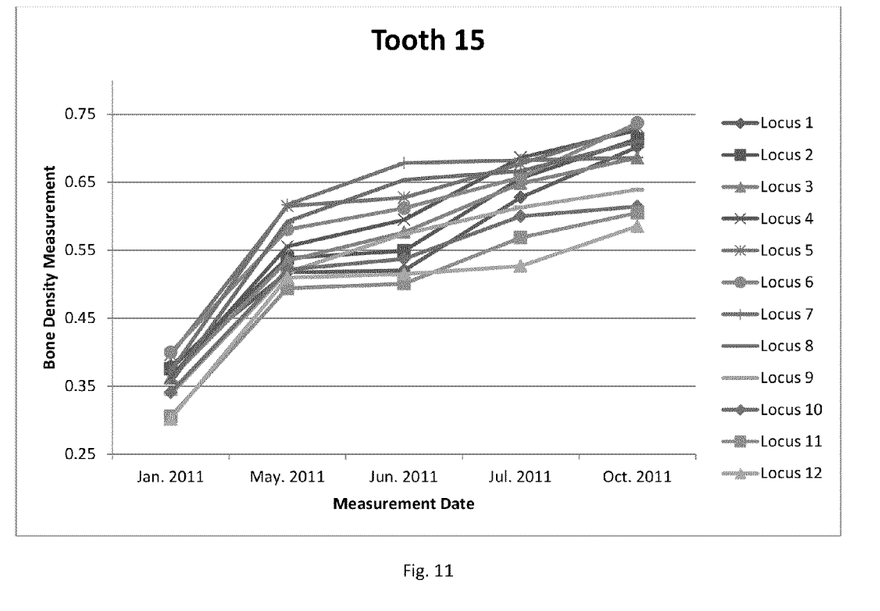
FIG. 11 shows bone density measurements for tooth 15 of a patient at 12 loci on the tooth following treatment with a soft tissue diode laser and a substrate over time.

Treatment was repeated on tooth 15 on four subsequent occasions, at which time the pocket depths at each loci were measured prior to treatment. Measurements are shown in FIG. 11. The data show an increase in calcium density at the specific loci.

II. Analysis of Tooth #12 at 17 Unique Loci

Figure 12:
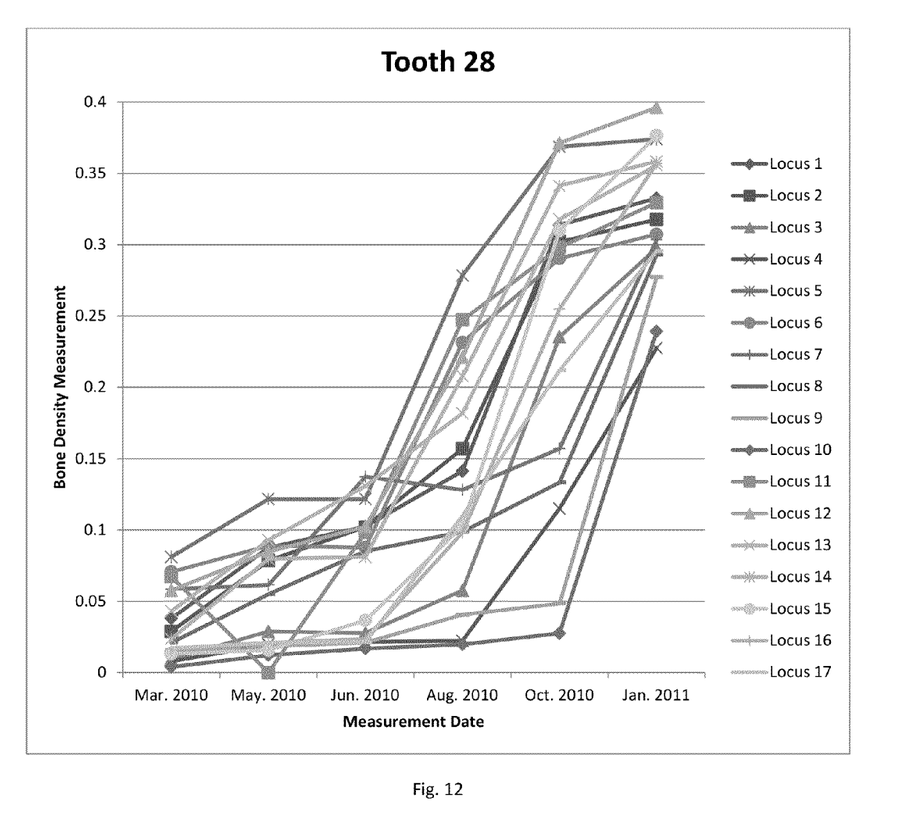
FIG. 12 shows bone density measurements for tooth 28 of a patient at 17 loci on the tooth following treatment with a soft tissue diode laser and a substrate over time.

A patient's pocket depths at tooth 28 were measured at 17 separate loci. The treatment disclosed herein was performed on five subsequent occasions, at which time the pocket depths at each loci were measured prior to treatment. Measurements are shown in FIG. 12. The data show an increase in calcium density across all loci.

III. Analysis of Tooth #2, #3 and #15 at 3 Unique Loci Per Tooth

Figure 13:
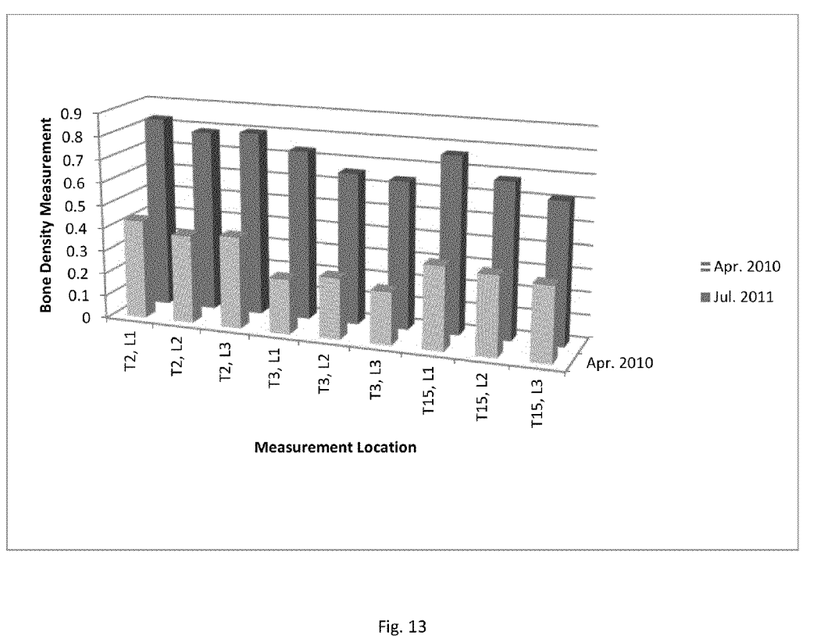
FIG. 13 shows bone density measurements for tooth 2, tooth 3 and tooth 15 of a patient at 3 loci per tooth following treatment with a soft tissue diode laser and a substrate over time.
Figure 14A:
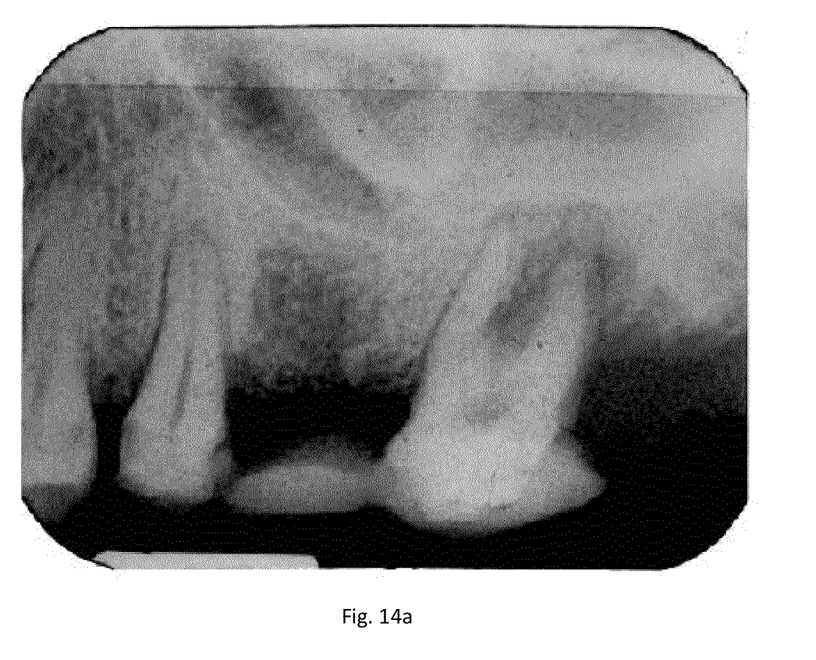
Figure 14B:
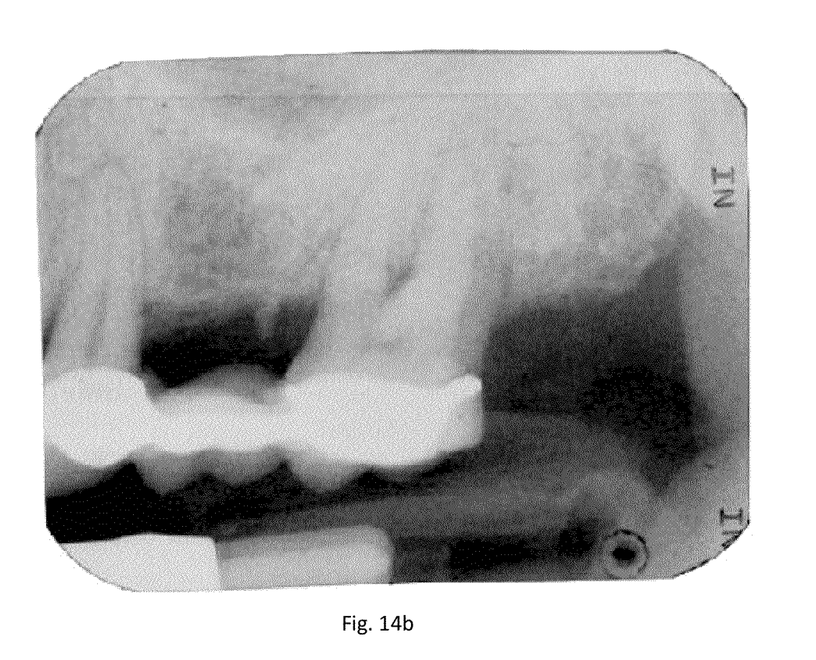
Figure 15A:
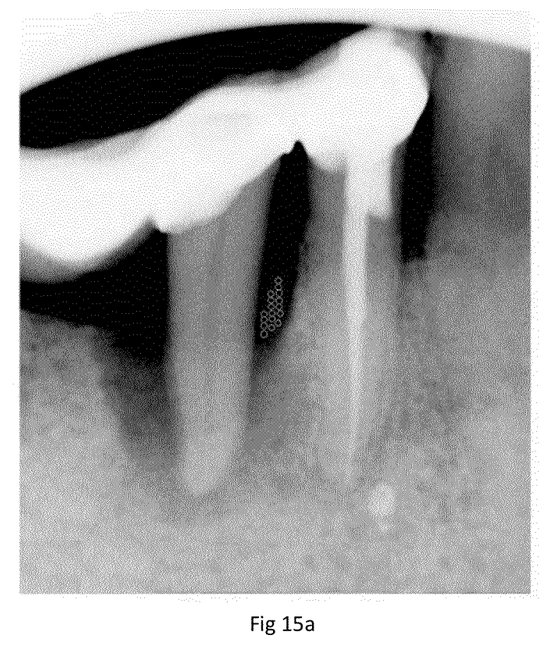
Figure 15B:
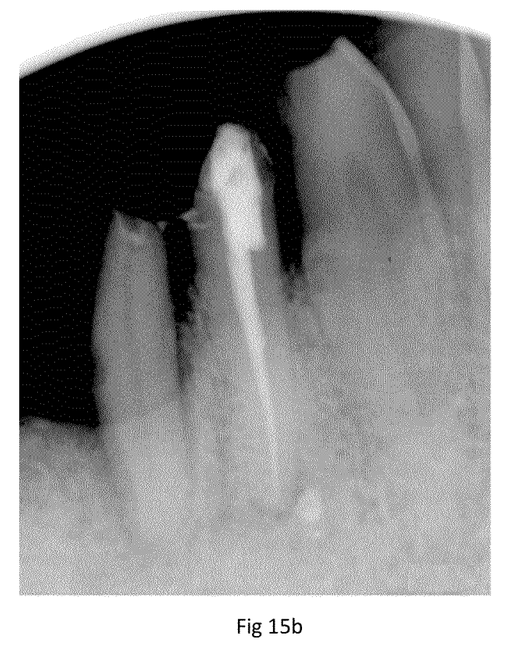
Figure 16A:
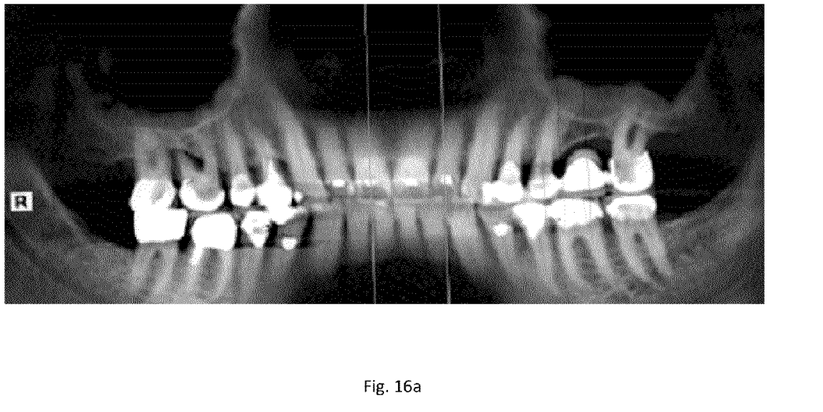
Figure 16B:
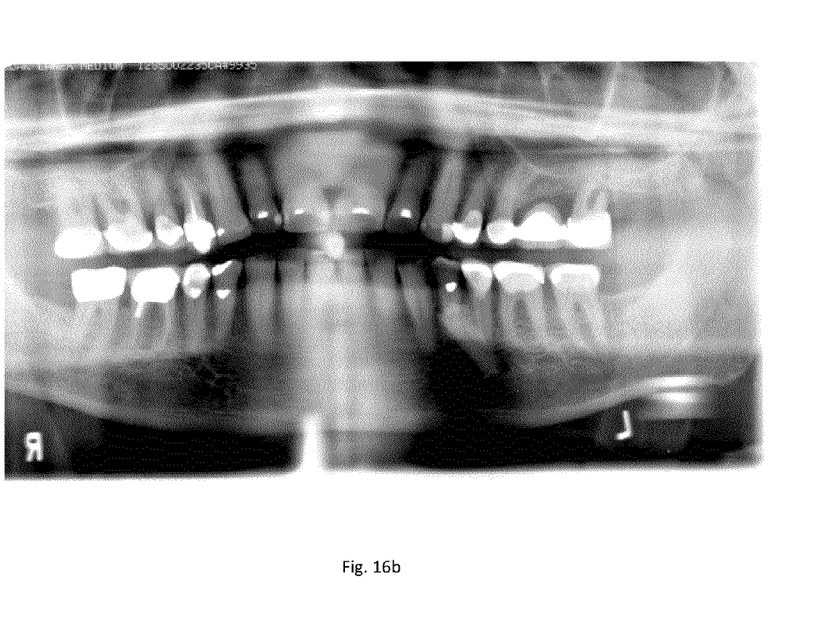

A patient's pocket depths at tooth 2, tooth 3 and tooth 15 were measured at three separate loci per tooth. The treatment disclosed herein was performed 3 months after the initial treatment, at which time the pocket depths at each loci were measured prior to treatment. Measurements are shown in FIG. 13. The data show a progression of bone generation.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed.

Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A substrate mixture for the treatment of gum disease, wherein the substrate mixture is comprised of:
   a) a first substrate; and
   b) a second substrate, wherein the first substrate is comprised of:
  a) between 40% and 80% sterile water
  b) 1.1% sodium chloride;
  c) 1% benzoic acid;
  d) 9% lysine;
  e) 9% proline;
  f) 9% essential amino acids, wherein the essential amino acids include equal parts isoleucine, leucine, methionine, phenylalanine, threonine, tryptophan, valine and histadine;
  g) 2% non-essential amino acids, wherein the non-essential amino acids include equal parts alanine, arginine, glutamate, glycine and serine;
  h) 2% phosphates, wherein the phosphates include equal parts adenosine diphospate (ADP), adenosine triphosphate (ATP), and acetylcholine; and
  i) 6.9% free bases, wherein the free bases include equal parts adenosine, uridine, guanosine, and cytidine.

2. The substrate mixture of claim 1, wherein the second substrate is comprised of:
  a) tricalcium phosphate; and
  b) hydroxyapatite crystals.

3. The substrate mixture of claim 1, wherein the first substrate includes aspartate in an equal amount relative to the other non-essential amino acids.

4. The substrate mixture of claim 1, wherein the first substrate includes aspartate in a greater amount relative to the other non-essential amino acids.

5. The substrate mixture of claim 1, wherein the substrate mixture has a pH of about 7.4.

6. The substrate mixture of claim 2, wherein the tricalcium phosphate is precipitated in calcium hydroxide and devil's claw oil.

7. The substrate mixture of claim 2, wherein the hydroxyapatite crystals are precipitated in calcium hydroxide and devil's claw oil.

8. The substrate mixture of claim 2, wherein the tricalcium phosphate is in the form of crystals.

9. The substrate mixture of claim 8, wherein the tricalcium phosphate crystals are 10-50 micro meter in size.

10. The substrate mixture of claim 8, wherein the tricalcium phosphate crystals are 50-150 micro meter in size.

11. The substrate mixture of claim 8, wherein the tricalcium phosphate crystals are 100-300 micro meter in size.

12. The substrate mixture of claim 8, wherein the tricalcium phosphate crystals are 500-1000 micro meter in size.

13. The substrate mixture of claim 8, wherein the tricalcium phosphate crystals are 1-3 mm in size.

14. The substrate mixture of claim 2, wherein the hydroxyapatite crystals are non-porous.

15. The substrate mixture of claim 2, wherein the hydroxyapatite crystals are porous.

16. The substrate mixture of claim 8, wherein the tricalcium phosphate crystals are non-porous.

17. The substrate mixture of claim 8, wherein the tricalcium phosphate crystals are porous.

* * * * *

UNITED STATES PATENT AND TRADEMARK OFFICE
CERTIFICATE OF CORRECTION

PATENT NO. : 9,180,319 B2
APPLICATION NO. : 13/864226
DATED : November 10, 2015
INVENTOR(S) : Kalmeta It is certified that error appears in the above-identified patent and that said Letters Patent is hereby corrected as shown below:

Title Page, Item (54) and in the Specification, Column 1, line 2: the word "OSSEUS" should read "OSSEOUS";

In the Drawings

Fig 10, in item 18, third line: the word "intermitten" should read "intermittent";

Fig, 10, in item 18, fifth line: the word "suclus" should read "sulcus";

In the Specification

Col. 1, line 18: insert the word --the-- after the word utilizes;

Col. 1, line 24: the word "Osseus" should read "Osseous";

Col. 1, line 58: insert the word --and-- before the word acquisition;

Col. 1, line 63: delete the "," after the word protocol;

Col. 2, line 34: delete the word "and" before the word green;

Col. 2, line 55: delete the ";" after the word oil;

Col. 3, line 29: the word "claim" should read "claims";

Col. 3, line 43: the word "alter" should read "after";

Col. 4, line 35: the word "as" should be replaced with "than";

Signed and Sealed this
Nineteenth Day of July, 2016

Michelle K. Lee
*Director of the United States Patent and Trademark Office*

CERTIFICATE OF CORRECTION (continued)
U.S. Pat. No. 9,180,319 B2

Col. 4, line 46: insert the word --and-- after the ",";

Col. 4, line 67: the word "planning" should read "planing";

Col. 5, line 1: the word "planning" should read "planing";

Col. 7, line 36: the word "include" should read "includes";

Col. 7, line 62: the word "planning" should read "planing"; and

Col. 7, line 64: the word "is" should be replaced with "was".